United States Patent [19]

Teed

[11] 4,325,372
[45] Apr. 20, 1982

[54] ELASTIC LEG DISPOSABLE DIAPER

[75] Inventor: Richard K. Teed, Greenwood, S.C.

[73] Assignee: Riegel Textile Corporation, Greenville, S.C.

[21] Appl. No.: 85,372

[22] Filed: Oct. 16, 1979

[51] Int. Cl.³ .............................................. A61F 13/16
[52] U.S. Cl. .................................................. 128/287
[58] Field of Search .................. 128/284, 287, 290 R, 128/288, 285; 112/121, 130

[56] References Cited

U.S. PATENT DOCUMENTS

| 28,139 | 8/1974 | Gore ..................................... | 156/547 |
| 3,616,770 | 11/1971 | Blyther et al. ...................... | 112/130 |
| 3,860,003 | 1/1975 | Buell .................................. | 128/287 |
| 3,984,272 | 10/1976 | Teed .................................. | 128/284 |
| 4,050,462 | 9/1977 | Woon et al. ........................ | 128/287 |
| 4,081,301 | 3/1978 | Buell .................................. | 128/287 |
| 4,205,679 | 6/1980 | Repke ................................ | 128/287 |

Primary Examiner—Robert W. Michell
Assistant Examiner—T. J. Wallen
Attorney, Agent, or Firm—Bell, Seltzer, Park & Gibson

[57] ABSTRACT

An improved elastic leg disposable diaper and process for manufacturing same; wherein the diaper includes elastic strips extending and being secured to the diaper continuously along the full length of the outside longitudinal edges of the diaper and wherein the elastic strips are secured in the crotch area in stretched elastically-contractible condition forming gathered and extendible side portions in the crotch area for elastic compliance of such side portions to the legs of the wearer.

2 Claims, 8 Drawing Figures

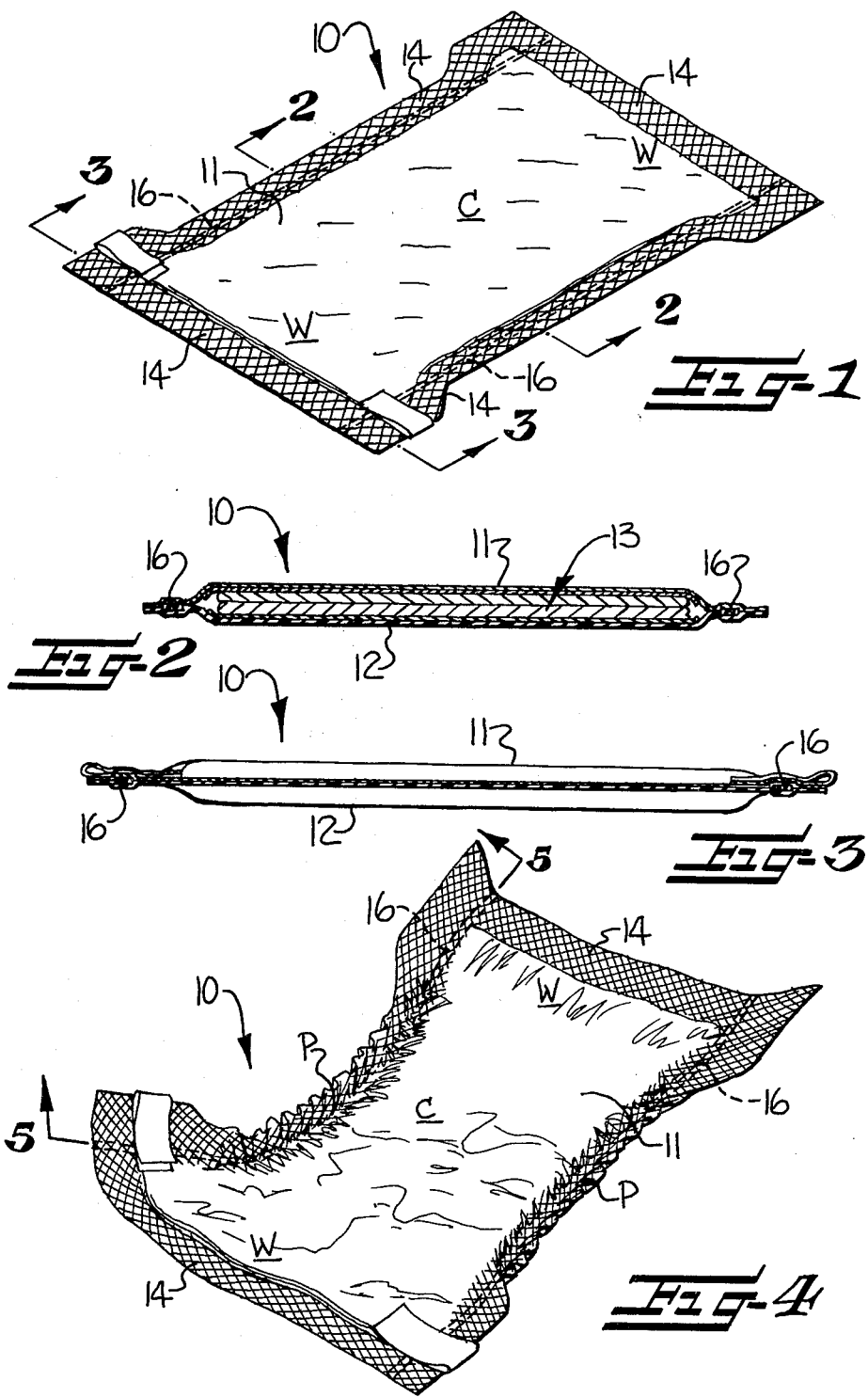

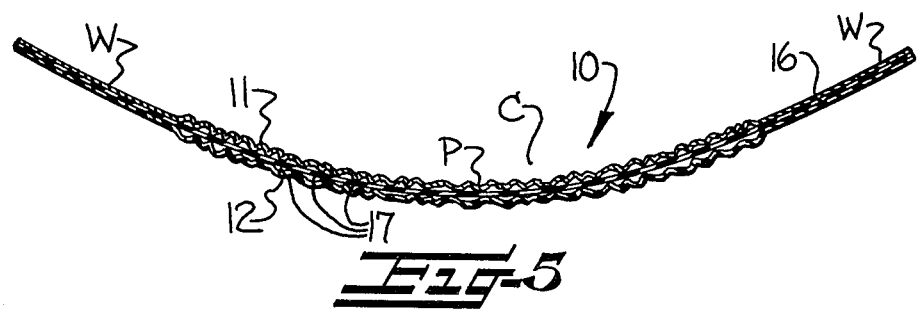
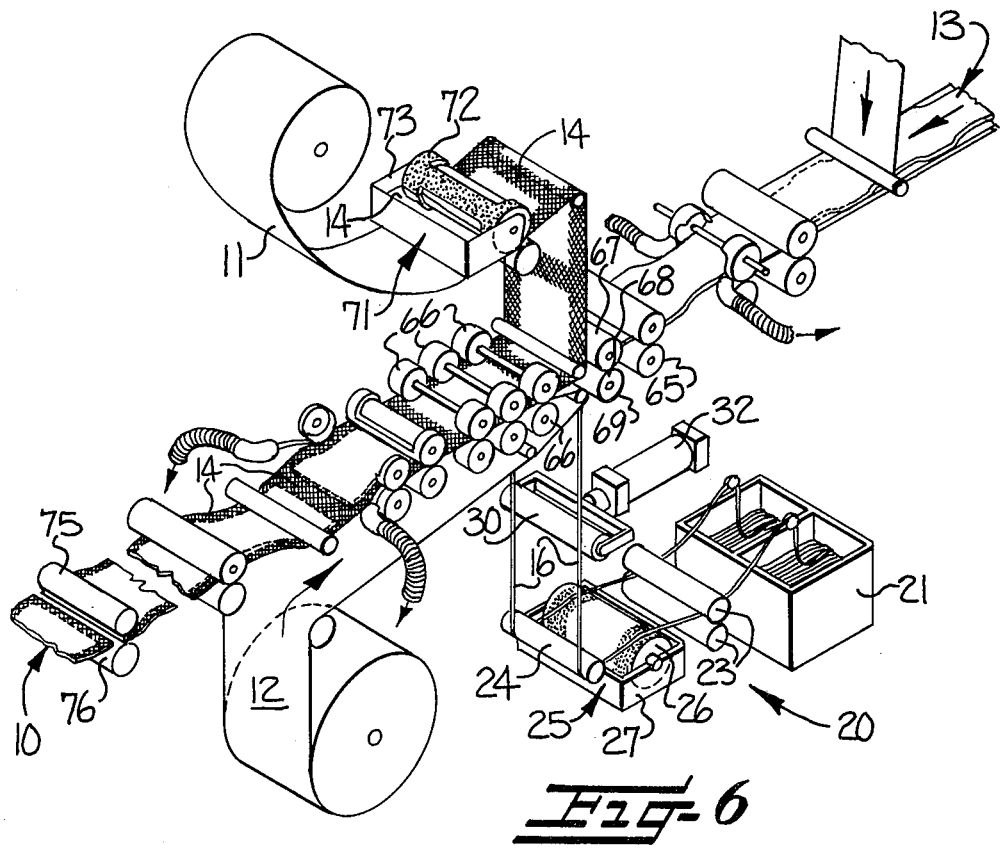

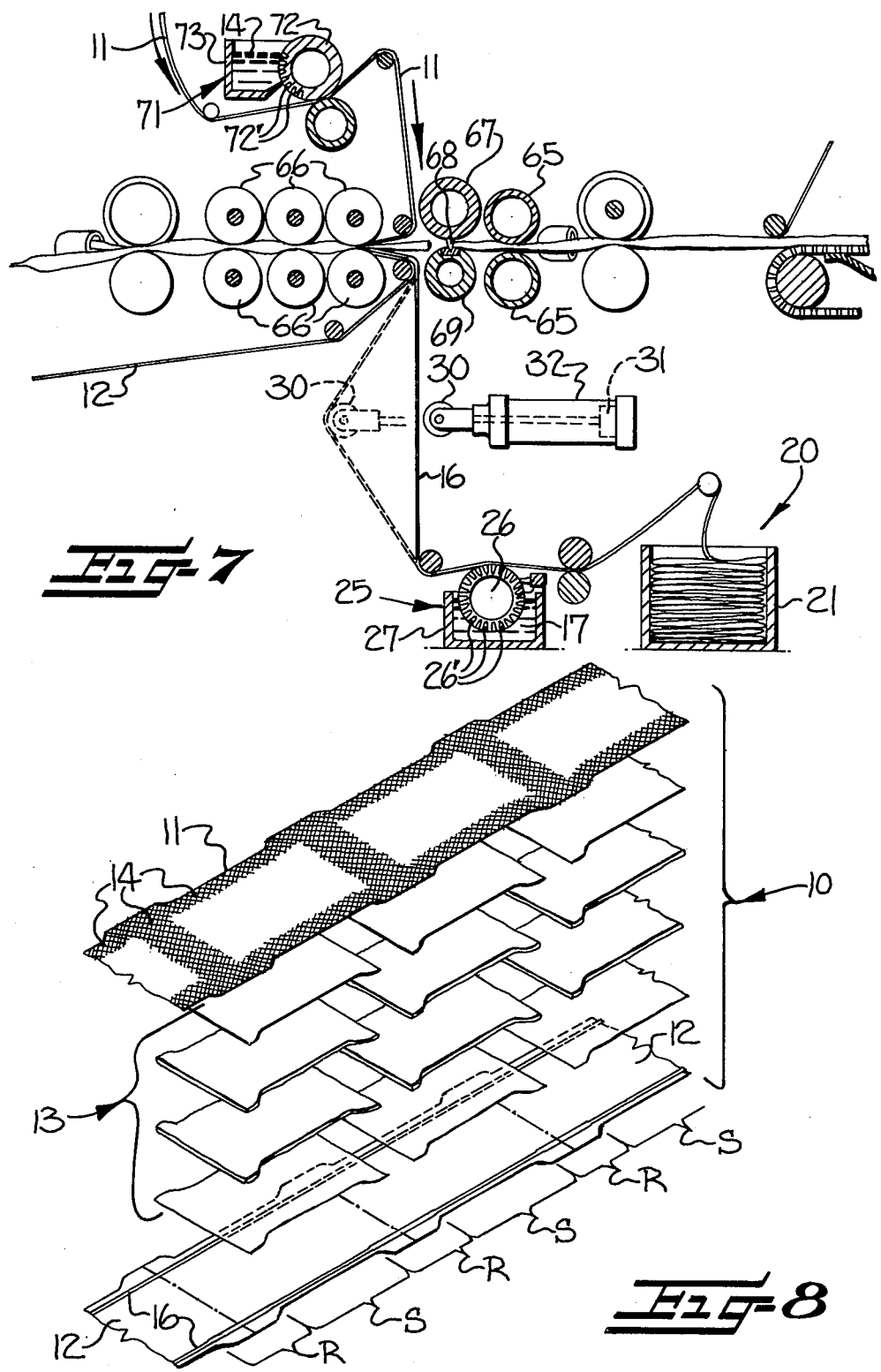

ELASTIC LEG DISPOSABLE DIAPER

FIELD OF THE INVENTION

This invention relates to an improved elastic leg disposable diaper and process for manufacturing same; wherein, the diaper includes elastic strips extending and being secured to the diaper continuously along the full length of the outside longitudinal edges of the diaper in a new and improved manner and wherein the elastic strips are secured in the crotch area in stretched elastically-contractible condition forming gathered and elastically-extendible side portions in the crotch area for elastic conformance of such side portions with the legs of the wearer.

BACKGROUND OF THE INVENTION

Over the past decade, disposable diapers, which include fluid-absorbent interior pads positioned between fluid-permeable top cover sheets and fluid-impermeable bottom cover sheets, have become increasingly popular. These disposable diapers are fabricated and sold in various shapes, sizes and constructions.

More recently, disposable diapers known in the trade as "elastic leg" disposable diapers have been introduced and are gaining popularity. These disposable diapers are preferably of generally hour-glass configuration including a central crotch-fitting area and outer waist-filling areas and have elastic strips secured along the outside longitudinal edges of the crotch area of the disposable diapers for forming extendible side portions along the crotch area of the diaper for elastic compliance to the legs of the wearer, such as has heretofore been available with waterproof panties utilized in diapering infants. Examples of commercial forms of such elastic leg diapers may be seen in The Procter & Gamble Company's U.S. Pat. No. 3,860,003 and Kimberly-Clark Corporation's U.S. Pat. No. 4,050,462.

Although the elastic leg disposable diapers commercialized under each of these two prior art patents are apparently successful in the marketplace, the diapers of these two prior art patents suffer from certain disadvantages relating to the manner in which the elastic strips are secured within the longitudinal edges of the diaper which result in structural deficiencies and an expensive and complicated procedure of inserting such elastic strips.

Although the Procter & Gamble U.S. Pat. No. 3,860,003 does not fully and clearly disclose the process utilized in inserting the elastic strips within the longitudinal edges of the disposable diaper, its subsequent U.S. Pat. No. 4,081,301 clearly discloses such process. As may be seen in this Procter & Gamble U.S. Pat. No. 4,081,301 and in the Kimberly-Clark U.S. Pat. No. 4,050,462, both of these elastic leg disposable diaper products involve the insertion of the elastic strips within the longitudinal edges of the disposable diaper being manufactured in serially-interconnected form by a process in which adhesive is intermittently applied to spaced-apart portions or lengths of continuous strips of elastic and the elastic strips are continuously stretched and secured within the longitudinal edges of the disposable diapers so that the portions of the elastic strips having adhesive thereon are secured within the crotch area of the diaper and the lengths of the elastic strips without adhesive thereon are positioned within the longitudinal edges of the outer waist areas of the diaper. With this construction, when the disposable diapers are cut apart into individual diapers and the elastic strips are cut, the portions of the elastic strips which are unsecured within the waist-fitting portions of the diaper will snap within the diaper leaving loose ends therein and the portion or lengths of the elastic strips secured within the crotch area of the diaper will gather such area forming extendible side portions.

As a result of the above manufacturing process, the snapping in of the loose or unsecured ends of the elastic strips at the outer waist-fitting areas of the diaper sometimes results in damage to the diaper and leaves open passages through the transverse edges of the diaper which may be susceptible to moisture leaks, etc. Also, this prior manufacturing process requires complicated and expensive equipment, such as that disclosed in the above-identified Procter & Gamble U.S. Pat. No. 4,081,301.

SUMMARY OF THE INVENTION

Accordingly, it is the object of this invention to provide an improved, elastic leg, disposable diaper and process for manufacturing same which overcomes the problems discussed above with prior elastic leg diaper products and their process for manufacture and provides an improved and simplified product and process.

By this invention, an improved elastic leg disposable diaper and process for its manufacture have been provided wherein the elastic strips are inserted and adhesively secured along the entire length of the outside longitudinal edges of the diaper and the elastic strips are intermittently stretched so that the strips are secured in the crotch area in stretched elastically-contractible condition forming gathered and extendible side portions in the crotch area. Preferably, the elastic strips are secured to the diaper in the waist area in less elastically-contractible or relaxed condition so as to provide less or no gathering in the side portions in the waist area. This is in contrast to the above discussed prior art elastic leg diapers wherein the elastic strips are intermittently adhesively secured and continuously stretched during the process.

In its broadest sense, the present invention recognizes for the first time that elastic strips may be continuously secured along the full length of the outside longitudinal edges of a disposable diaper, wherein the elastic strips are secured in the crotch area in stretched elastically-contractible condition forming gathered and extendible side portions in the crotch area for elastic compliance to the legs of the wearer. This contrasts with the prior art forms of elastic leg diapers having elastic strips secured to the longitudinal edges only in the waist area of the disposable diaper and having loose ends thereon.

The product and process of this invention eliminate the problems and disadvantages discussed above and provide a simplified product and process, as will be discussed in more detail in the detailed description of this invention to follow.

BRIEF DESCRIPTION OF THE DRAWINGS

Some of the objects and advantages of this invention having been set forth, other objects and advantages will appear when taken in conjunction with the accompanying drawings in which:

FIG. 1 is a perspective view of the improved elastic leg disposable diaper of this invention in flat condition with the side portions of the crotch area in an extended position;

FIG. 2 is a cross sectional view taken through the crotch area of the diaper and generally along the line 2—2 of FIG. 1;

FIG. 3 is a cross sectional view taken through one of the outer waist areas of the diaper and generally along the line 3—3 of FIG. 1;

FIG. 4 is a top perspective view of the diaper of FIG. 1 with the side portions of the crotch area in relaxed, gathered and extendible position;

FIG. 5 is a cross sectional view taken through one of the longitudinal edges of the relaxed diaper of FIG. 4 and generally along the line 5—5 of FIG. 4;

FIG. 6 is a schematic view illustrating apparatus which is capable of practicing the improved process of this invention;

FIG. 7 is a schematic side elevational view of a portion of the apparatus of FIG. 6; and FIG. 8 is an exploded view of the components of the elastic leg disposable diaper produced by the process of this invention in serially-interconnected form prior to being cut apart in individual diapers and showing the lengths of the elastic strips in stretched and relaxed conditions, respectively, as the strips are inserted into the serially-interconnected diapers during manufacture.

DETAILED DESCRIPTION OF THE INVENTION

In the drawings, FIGS. 1-5 illustrate the improved elastic leg disposable diaper and FIGS. 6-8 illustrate the improved process of this invention.

Referring firstly to FIGS. 1-5, the improved elastic leg disposable diaper, generally indicated at 10, is preferably of generally hour-glass configuration and has a central crotch-fitting area C and outer waist-fitting areas W designed to be placed around the crotch and waist of the wearer when the diaper 10 is placed on the wearer in conventional manner.

The diaper 10 further includes a fluid-permeable top cover sheet 11, which may be of any suitable construction conventionally utilized in disposable diaper and other absorbent article constructions for being positioned in contact with the wearer of the disposable diaper 10 for receiving and passing therethrough body fluids of the wearer. The diaper 10 further includes a fluid-impermeable bottom cover sheet 12, which may be constructed of plastic or other suitable material conventionally utilized in such disposable diaper and other disposable absorbent article constructions for being positioned away from the wearer for preventing the body fluids of the wearer from passing out of the disposable diaper 10. Positioned between the top cover sheet 11 and the bottom cover sheet 12 is a fluid-absorbent interior pad 13 for absorbing body fluids of the wearer. As illustrated in FIG. 2, this interior absorbent pad 13 may include two layers or may be a single layer or any other suitable construction conventionally utilized in such disposable diaper constructions.

The disposable diaper 10 is secured along its longitudinal and transverse edges by suitable adhesive or other attachment means 14 which secures the top sheet 11 to the bottom sheet 12 and generally provides an envelope around the interior pad which is unsecured at its longitudinal edges and in the central crotch area C to either the top cover sheet or bottom cover sheet to allow the pad to conform to the shape of the diaper when placed in position on the wearer.

The diaper 10 further includes elastic strips 16 extending and being secured by adhesive or other suitable means 17, see FIG. 5, to the diaper 10 continuously along the full length of the outside longitudinal edges of the diaper, as indicated in FIGS. 1, 4 and 5. These elastic strips, as will be explained in detail below, are secured in the crotch area C in stretched elastically-contractible condition forming gathered and extendible side portions P in the crotch area C, as shown in FIGS. 4 and 5, for elastic compliance to the legs of the wearer. Preferably, the elastic strips 16 are secured in the waist areas W in less elastically-contractible or relaxed condition so as to provide less or no gathering of the side portions of the waist areas W, as indicated in FIGS. 4 and 5.

As may be clearly seen in FIGS. 1 and 2, the interior absorbent pad 13 extends to close proximity with and within approximately ¾ of an inch of the elastic strips 16 on both of the longitudinal sides of the diaper 10 to provide fluid absorbency in the elastically-contractible side portions P of the diaper 10.

Considering now the improved process of this invention, reference may be had to FIGS. 6 and 7 which show schematically portions of an apparatus suitable for use in the process of producing the improved elastic leg diapers 10 of the present invention. Full details of mechanical connections, drives, etc. are not illustrated and will not be described herein for purposes of clarity. However, details of the construction and operation of apparatus for assembling such diapers may be seen in co-pending application Ser. No. 046,114, filed June 6, 1979 and prior U.S. Pat. No. Re. 28,139 and U.S. Pat. No. 3,984,272, all of which are assigned to the assignee of the present invention. It is noted that the apparatus for inserting elastic strips into the longitudinal edges of the elastic leg disposable diapers produced by the apparatus in accordance with assignee's co-pending U.S. patent application Ser. No. 046,114 includes apparatus operating under the general principles of the identified prior art patents of The Procter & Gamble Company and Kimberly-Clark Corporation and the process of the present invention is a specific improvement thereover.

Referring now to the apparatus illustrated in FIGS. 6 and 7, interconnected multi-layer absorbent pads 13, constructed in accordance with disclosure of applicant's co-pending U.S. patent application Ser. No. 046,114 or otherwise, are fed through pairs of driven feed rolls 65, 66 between which is provided a pad severing means in the form of a rotating cutting roll 67 having a knife blade 68 thereon and an anvil roll 69 which operate to intermittently cut the interconnected multi-layer pads 13 transversely for separation of the interconnected pads 13. The driven feed rolls 66 are driven somewhat faster than the driven feed rolls 65 to effect an overfeeding of the severed multi-layer absorbent pads 13 for spacing the pads apart in the further fabrication of the disposable diapers.

Immediately prior to the feed rolls 66, the top cover sheet 11 is fed from a suitable source of supply to feed rolls 66 and through a glue applicator 71 which applies the glue or adhesive 14 of a suitable type in a predetermined pattern transversely across the cover sheet 11 at spaced locations and along the longitudinal edges of the top cover sheet 11 for purposes of gluing the transverse and longitudinal edges of the ultimately fabricated disposable diaper 10 together. Glue applicator 71 may comprise any suitable glue applicator for the above purpose and as illustrated herein may include a glue applicator roll 72 having indentations or cups 72' therein which collectively are of the predetermined configuration of the areas for receiving adhesive 14. The applicator roll 72 may pass through an adhesive supply tank 73 for containing a supply of the adhesive 14.

Simultaneously with the above, the bottom cover sheet 12 is fed from a source of supply to feed rolls 66 and into superimposed position under the spaced-apart interior pads 13 and top cover sheet 11 so that all of these components are in superimposed position. The top cover sheet 11 and bottom cover sheet 12 are pressed into contact with each other by the feed rolls 66 and subsequent rolls and are adhesively secured together along longitudinal edges and transversely between the separated and spaced-apart absorbent pads 13 to form serially-interconnected disposable diapers 10.

These serially-interconnected diapers are fed through a series of mechanisms, not shown, and are ultimately fed between cutter roll 75 and anvil roll 76 which cut the serially-interconnected diapers 10 transversely between interior pads to form individual diapers 10.

For cooperating with the above-described apparatus and process for manufacturing disposable diapers 10, the present invention has provided an improved process utilizing apparatus, generally indicated at 20, for inserting the elastic strips 16 into the longitudinal edges of the disposable diapers 10 during the above-described manufacture and assembly of the diaper 10.

This means 20 for inserting the elastic strips 16 comprises means for feeding continuous elastic strips 16 from a supply 21 into desired position between feed rolls 66 in contact with the longitudinal edges of the serially-interconnected diapers for adhesive securement therebetween. This feeding means may include driven feed rolls 23 and feed rolls 66 between which the elastic strips are fed. As may be seen in FIGS. 6 and 7, the elastic strips are thus inserted along the longitudinal edges of the serially-interconnected diapers 10 at the point in which the top cover sheet 11, bottom cover sheet 12 and spaced-apart interior pads 13 are brought into superimposed position with each other or at the feed rolls 66.

The elastic strips 16 may include a fast acting contact adhesive coating or other type of adhesive already on the strips 16 or such adhesive may be applied by an applicator device 25 which includes an adhesive applicator roll 26 passing through a trough 27 of fast acting adhesive and having indentations or cups 26' therein for picking up and applying adhesive continuously along the elastic strips 16. Regardless of how the adhesive is applied, it is important that the adhesive be fast acting since the elastic strips are being secured in both stretched and relaxed conditions as will be discussed below.

The elastic strip inserting means 20 further includes means for alternately stretching and relaxing predetermined lengths of the continuous elastic strips in timed relationship to the feeding thereof by the feeding means so that the stretched lengths of elastic strips will be adhered to the crotch area C and the substantially relaxed lengths of elastic strips 16 will be adhered to the waist areas W continuously along the longitudinal edges of the serially-interconnected diapers 10. This is clearly indicated in FIG. 8 wherein the portions or lengths of the elastic strips 16 indicated by the brackets R are relaxed portions and are secured to the longitudinal edges of the waist areas W of the serially-interconnected diapers 10 and the portions or lengths of the elastic strips indicated by the brackets S are stretched portions and are secured to the longitudinal edges of the crotch areas C of the serially-interconnected diapers 10.

The means for alternately stretching and relaxing the predetermined lengths of the elastic strips is shown schematically herein as including the roll 30 connected to the end of a piston and cylinder device 31, 32 which, in turn, is suitably operated and controlled by a device (not shown) which will alternately move the roll 30 into and out of engagement with the elastic strips 16 for intermittently stretching and relaxing the elastic strips 16 so that intermittent stretched and relaxed portions or lengths S and R of the elastic strips 16 will be presented to the above-described diaper assembly machine in position within the longitudinal edges of the diaper as it is being assembled. The specific design and operation of the mechanism for alternately stretching and relaxing the elastic strips 16 does not form a part of the present invention however, reference may be had to commonly assigned U.S. Pat. Nos. 4,239,578 and 4,261,782, which were co-pending with the present application, for disclosure of such mechanisms.

Thus, this invention has provided an improved elastic leg disposable diaper and process for manufacturing same which overcomes problems presented with prior art forms of such diaper and the process and apparatus involved particularly with the insertion of the elastic strips therein.

In the drawings and specification, there have been set forth preferred embodiments of the invention and although specific terms are employed, they are used in a generic and descriptive sense only and not for purposes of limitation.

What is claimed is:

1. An improved elastic leg disposable diaper of generally hour-glass configuration providing longitudinal edge portions on opposite sides and transverse edge portions on opposite ends and defining between said longitudinal edge portions outer waist-fitting areas and a central crotch-fitting area of reduced width, said diaper comprising:

a fluid-permeable top cover sheet;

a fluid-impermeable bottom cover sheet;

a fluid-absorbent interior pad positioned between said top and bottom cover sheets;

an elastic strip extending and being secured to said diaper along the full length of each of said longitudinal edge portions and along said central crotch-fitting area and said waist-fitting areas of said diaper, and wherein each of said elastic strips are secured in said crotch-fitting area in stretched elastically-contractible condition forming gathered and extendible side portions in said crotch-fitting area when said elastic strips are relaxed for elastic conformance with the legs of the wearer and are secured in said waist-fitting areas in less stretched elastically-contractible or substantially relaxed condition than in said crotch-fitting area so as to provide less or no gathering of the side portions in said waist-fitting areas compared to said crotch-fitting area; and means securing said top cover sheet and said bottom cover sheet to each other along the full length of said longitudinal edge portions and said transverse end portions for effectively sealing said diaper around the periphery thereof to eliminate open passageways which may cause leaking from the interior of said diaper.

2. An improved elastic leg disposable diaper, as set forth in claim 1, in which said fluid-absorbent interior pad extends to within ¾ of an inch of said elastic strips and is unsecured to said top cover sheet and said bottom cover sheet in said crotch area.

* * * * *

UNITED STATES PATENT AND TRADEMARK OFFICE
CERTIFICATE OF CORRECTION

PATENT NO. : 4,325,372
DATED : April 20, 1982
INVENTOR(S) : Richard K. Teed

It is certified that error appears in the above-identified patent and that said Letters Patent are hereby corrected as shown below:

Column 1, line 28, "filling" should be --fitting--.

Signed and Sealed this

Seventh Day of September 1982

[SEAL]

Attest:

GERALD J. MOSSINGHOFF

Attesting Officer Commissioner of Patents and Trademarks